| (12) | United States Patent | (10) Patent No.: | US 10,542,740 B2 |
|---|---|---|---|
| | Kashima et al. | (45) Date of Patent: | Jan. 28, 2020 |

(54) DEVICE AND METHOD FOR VAPORIZING/DISCHARGING CHEMICAL AGENT

(71) Applicant: DAINIHON JOCHUGIKU Co., Ltd., Osaka (JP)

(72) Inventors: Seiichi Kashima, Osaka (JP); Ryoko Ukita, Osaka (JP); Yumi Kawajiri, Osaka (JP); Koji Nakayama, Osaka (JP)

(73) Assignee: DAINIHON JOCHUGIKU Co., Ltd., Osaka (JP)

( * ) Notice: Subject to any disclaimer, the term of this patent is extended or adjusted under 35 U.S.C. 154(b) by 216 days.

(21) Appl. No.: 15/527,025

(22) PCT Filed: Dec. 14, 2015

(86) PCT No.: PCT/JP2015/084873
§ 371 (c)(1),
(2) Date: May 16, 2017

(87) PCT Pub. No.: WO2016/098712
PCT Pub. Date: Jun. 23, 2016

(65) Prior Publication Data
US 2017/0325442 A1 Nov. 16, 2017

(30) Foreign Application Priority Data

Dec. 15, 2014 (JP) ................... 2014-253418

(51) Int. Cl.
*A01M 1/20* (2006.01)
*A01N 25/08* (2006.01)
(Continued)

(52) U.S. Cl.
CPC ........ *A01M 1/2055* (2013.01); *A01M 1/2033* (2013.01); *A01N 25/08* (2013.01);
(Continued)

(58) Field of Classification Search
CPC ... A01M 1/2055; A01N 25/08; A61L 2202/15
See application file for complete search history.

(56) References Cited

U.S. PATENT DOCUMENTS

2007/0148051 A1 6/2007 Katsuda et al.

FOREIGN PATENT DOCUMENTS

| JP | 5-68459 | 3/1993 |
|---|---|---|
| JP | 11-92303 | 4/1999 |

(Continued)

OTHER PUBLICATIONS

English Translation of Japanese Document No. JP 2006 025656 provided by the European Patent Office website espacenet.com: Kimura Takeo; Chemical Support; Feb. 2, 2006 (Year: 2006).*

(Continued)

*Primary Examiner* — Kevin Joyner
(74) *Attorney, Agent, or Firm* — Renner, Otto, Boisselle & Sklar, LLP (57) ABSTRACT

Provided is a chemical agent vaporizing/discharging device which can efficiently vaporize and discharge a chemical agent from a chemical agent retainer, and sufficiently diffuse the chemical agent, even when the device is used in a relatively large space or outdoors. A chemical agent vaporizing/discharging device 100 comprises: a chemical agent retainer 50 having a chemical agent retention layer 10 including interstices 11 for allowing retention of a volatile chemical agent, and a gas permeable layer 20 including voids 21 having a size larger than a size of the interstices 11; and a rotational drive part 60 for driving the chemical agent retainer 50. A shape and a size of the chemical agent retainer 50, and a rotational speed of the rotational drive part 60, are set so that a centrifugal effect of 10 to 150 (G) is obtained during rotation of the chemical agent retainer 50.

6 Claims, 3 Drawing Sheets

(51) Int. Cl.
  *A01N 53/00*   (2006.01)
  *A01N 25/34*   (2006.01)
  *A01N 25/18*   (2006.01)
(52) U.S. Cl.
  CPC ............ *A01N 25/34* (2013.01); *A01N 53/00* (2013.01); *A01N 25/18* (2013.01)

(56) References Cited

FOREIGN PATENT DOCUMENTS

| | | |
|---|---|---|
| JP | 2006-25656 | 2/2006 |
| JP | 2011-92016 | 5/2011 |
| JP | 2012-005355 | 1/2012 |

OTHER PUBLICATIONS

Decision of Refusal issued to corresponding Japanese Patent Application No. 2016-564835 dated Sep. 4, 2018 along with English translation of a main part thereof.
First Examination report issued to corresponding Australian Patent Application No. 2015364877 dated Apr. 30, 2018.
First Office Action issued to corresponding Japanese Patent Application No. 2016-564835 dated Jun. 5, 2018.
First Office Action issued to corresponding Korean Patent Application No. 10-2017-7013489 dated May 18, 2018.
PCT/JP2015/084873; PCT International Search Report of the International Searching Authority dated Feb. 10, 2016 and its English translation.
Office Action dated Nov. 10, 2016 issued to the corresponding Taiwanese patent application No. 104140675 along with the English translation of the main body.

\* cited by examiner

DEVICE AND METHOD FOR VAPORIZING/DISCHARGING CHEMICAL AGENT

The present application is a U.S. National Stage Application based on and claiming benefit and priority under 35 U.S.C. § 371 of International Application No. PCT/JP2015/084873, filed 14 Dec. 2015, which in turn claims benefit of and priority to Japanese Application No. 2014-253418 filed 15 Dec. 2014, the entirety of both of which is hereby incorporated herein by reference.

TECHNICAL FIELD

The present invention relates to methods and devices for vaporizing and discharging a volatile chemical agent into the air.

BACKGROUND ART

In order to control insect pests, chemical agent vaporizing/discharging devices for vaporizing and discharging into space a chemical agent capable of repelling or killing insect pests have been commercialized. For example, known is a device which retains a volatile chemical agent in a diffusion member (chemical agent retainer), and drives the diffusion member using a drive means to vaporize and discharge the chemical agent into the air (see, for example, Patent Document 1). Patent Document 1 indicates that the diffusion member is configured in the shape of a fan in order to enhance the capability to vaporize and discharge the chemical agent, and the diffusion member is heated in order to vaporize and discharge a larger amount of the chemical agent.

Also known is the use of a honeycomb structure having multiple cells with both open ends having a cell size of 2 to 5 mm as a chemical agent retention carrier (chemical agent retainer) (see, for example, Patent Document 2). Patent Document 2 indicates that the honeycomb structure serving as a chemical agent retention carrier ensures a large area for retaining a chemical agent, and can reduce drag acting on a flow of air passing through the chemical agent retention carrier.

CITATION LIST

Patent Literature

Patent Document 1: Japanese Unexamined Patent Application Publication No. H05-68459
Patent Document 2: Japanese Unexamined Patent Application Publication No. H11-92303

SUMMARY OF INVENTION

Technical Problem

Most chemical agent vaporizing/discharging devices are mainly used indoors. Due to recent changes in housing, a space in which a chemical agent vaporizing/discharging device is used tends to increase. There is an increasing demand for use of a chemical agent vaporizing/discharging device not only in a living room etc. of a house, but also in a relatively large space such as an office, shop, workplace, or the like, and outdoors.

In this regard, the subject matter disclosed in Patent Document 1 and Patent Document 2 is not intended for use in a large space or outdoors. Patent Document 1 indicates that the chemical agent retainer is used in a space such as a living room of an ordinary house (see paragraph [0029] of Patent Document 1). Patent Document 2 indicates an example in which the chemical agent retainer was subjected to an insect pest control test in a living room having an area of six Jyos (Jyo is a Japanese unit of area: 1 Jyo is equal to about 1.7 m$^2$) (see paragraph [0032] in Patent Document 2). Thus, the subject matter disclosed in Patent Document 1 and Patent Document 2 is used in a living room of a typical house or the like, and therefore, when it is used in a relatively large space or outdoors, the effect of vaporizing and discharging a chemical agent may not be sufficient.

With the above in mind, the present invention has been made. It is an object of the present invention to provide a device and method for vaporizing and discharging a chemical agent which are capable of efficiently vaporizing and discharging the chemical agent from a chemical agent retainer, and sufficiently diffusing the chemical agent, even when it is used in a relatively large space or outdoors.

Solution to Problem

To achieve the above object, a chemical agent vaporizing/discharging device according to the present invention comprises:
a chemical agent retainer having a chemical agent retention layer including interstices for allowing retention of a volatile chemical agent, and a gas permeable layer including voids having a size larger than a size of the interstices; and
a rotational drive part for driving the chemical agent retainer,
wherein
a shape and a size of the chemical agent retainer, and a rotational speed of the rotational drive part, are set so that a centrifugal effect of 10 to 150 (G) is obtained during rotation of the chemical agent retainer.

In order to increase the efficiency of vaporization and discharging of a volatile chemical agent in a chemical agent retainer, typically, the chemical agent retainer may be rotated to generate an air flow as disclosed in Patent Document 1, or an air flow may be impinged on the chemical agent retainer using a fan as disclosed in Patent Document 2, or the like. In the conventional art, for example, in the case of Patent Document 1, it is considered that a great centrifugal force needs to be exerted on the chemical agent retainer. However, according to the results of recent study conducted by the present inventors, it is not always necessary or effective to simply increase the speed of revolution of the chemical agent retainer or the air blowing power, or increase the size of the chemical agent retainer, and thereby increase a centrifugal force exerted on the chemical agent retainer, in order to increase the efficiency of vaporization and discharging of a volatile chemical agent from a chemical agent retainer, and various settings should be made in order to obtain a suitable centrifugal effect in the chemical agent retainer. This is why, in the present invention, the chemical agent vaporizing/discharging device has the above configuration.

In the chemical agent vaporizing/discharging device having this feature, the chemical agent retainer has a chemical agent retention layer including interstices for allowing retention of a volatile chemical agent, and a gas permeable layer including voids having a size larger than a size of the interstices. Therefore, the volatile chemical agent retained in the interstices of the chemical agent retention layer is moved to the voids of the gas permeable layer, in which the chemical agent is easily vaporized and discharged into the air. In this state, when the chemical agent retainer is rotated by the rotational drive part, the volatile chemical agent is vaporized and discharged into the air. At this time, a shape and a size of the chemical agent retainer, and a rotational speed of the rotational drive part, are set so that a centrifugal effect of 10 to 150 (G) is obtained in the chemical agent retainer. Therefore, the volatile chemical agent retained in the chemical agent retainer is efficiently vaporized and discharged into the air, and sufficiently diffused. Therefore, even when the chemical agent vaporizing/discharging device having this configuration is used in a relatively large space or outdoors, the effect of the volatile chemical agent can be sufficiently exerted.

In the chemical agent vaporizing/discharging device of the present invention, the chemical agent retainer is preferably set so that the ratio (P=A/B) of a thickness (A) of the gas permeable layer to a thickness (B) of the chemical agent retention layer is more than 1.5 and not more than 50, and the rotational speed of the rotational drive part is preferably set so that a centrifugal vaporizing/discharging index (T=G/P) obtained by dividing the centrifugal effect (G) by the ratio (P) is more than 1.1 and less than 22.

In the chemical agent vaporizing/discharging device having this feature, the ratio (P=A/B) of the thickness (A) of the gas permeable layer to the thickness (B) of the chemical agent retention layer in the chemical agent retainer, and the centrifugal vaporizing/discharging index (T=G/P) in the rotational drive part, are set with respective suitable ranges. Therefore, the volatile chemical agent retained in the chemical agent retainer can be more efficiently vaporized and discharged and sufficiently diffused into the air. Therefore, even when the chemical agent vaporizing/discharging device having this feature is used in a relatively large space or outdoors, the effect of the volatile chemical agent can be reliably exerted.

In the chemical agent vaporizing/discharging device of the present invention, the chemical agent retainer is preferably a laminate of the chemical agent retention layer and the gas permeable layer, and the chemical agent retention layer is preferably provided one or both sides of the gas permeable layer in a lamination direction.

In the chemical agent vaporizing/discharging device having this feature, a suitable laminate of the chemical agent retention layer and the gas permeable layer forms the chemical agent retainer. Therefore, the volatile chemical agent retained in the chemical agent retention layer can be efficiently vaporized and discharged into the air, and sufficiently diffused, while the gas permeability of the gas permeable layer is maintained.

In the chemical agent vaporizing/discharging device of the present invention, the chemical agent retainer preferably has a form maintenance layer for maintaining a form of the gas permeable layer, the form maintenance layer being disposed adjacent to the gas permeable layer.

In the chemical agent vaporizing/discharging device having this feature, a form of the gas permeable layer is maintained by the form maintenance layer provided adjacent to the gas permeable layer, and therefore, the gas permeability of the chemical agent retainer can be sufficiently ensured. Therefore, the chemical agent vaporizing/discharging device can be used until substantially all the volatile chemical agent retained in the chemical agent retainer is vaporized and discharged into the air, i.e. used up.

In the chemical agent vaporizing/discharging device of the present invention, the chemical agent retainer is preferably in the shape of a disc perpendicular to an axis of rotation.

In the chemical agent vaporizing/discharging device having this feature, the chemical agent retainer is in the shape of a disc perpendicular to an axis of rotation, i.e. the chemical agent retainer has a reduced thickness, and therefore, the chemical agent vaporizing/discharging device has excellent portability.

In the chemical agent vaporizing/discharging device of the present invention, the chemical agent retainer is preferably in the shape of a hollow cylinder parallel to an axis of rotation.

In the chemical agent vaporizing/discharging device having this feature, the chemical agent retainer is in the shape of a hollow cylinder parallel to an axis of rotation. Therefore, all points along the length direction on the chemical agent retention layer are equidistant from the axis of rotation, and therefore, substantially the same centrifugal effect is exerted on the volatile chemical agent at every point on the chemical agent retention layer. As a result, the chemical agent vaporizing/discharging effect can be exerted substantially uniformly all the way around the chemical agent retainer.

In the chemical agent vaporizing/discharging device of the present invention, the chemical agent retainer is preferably housed in a rotating cartridge coupled to the rotational drive part.

In the chemical agent vaporizing/discharging device having this feature, the chemical agent retainer is rotated by the rotational drive part while the chemical agent retainer is housed in the rotating cartridge. Therefore, the chemical agent retainer is inhibited from being deformed by a centrifugal force. As a result, variations in the centrifugal effect during rotation of the chemical agent retainer can be reduced.

In the chemical agent vaporizing/discharging device of the present invention, the volatile chemical agent preferably contains a pyrethroid compound having a vapor pressure of $2\times10^{-4}$ to $1\times10^{-2}$ mmHg at 30° C.

In the chemical agent vaporizing/discharging device having this feature, a pyrethroid compound having a suitable vapor pressure is used as the volatile chemical agent. Therefore, the centrifugal effect of the chemical agent retainer allows the pyrethroid compound to be efficiently vaporized and discharged into the air, and sufficiently diffused.

To achieve the above object, a chemical agent vaporizing/discharging method according to the present invention is for vaporizing and discharging a volatile chemical agent into the air by rotating a chemical agent retainer retaining the volatile chemical agent. The method comprises:

a rotation adjustment step of adjusting a rotational speed of the chemical agent retainer to obtain a centrifugal effect of 10 to 150 (G).

In the chemical agent vaporizing/discharging method having this feature, excellent effects similar to those of the chemical agent vaporizing/discharging device of the present invention described above can be obtained.

Specifically, in the rotation adjustment step of adjusting the rotational speed of the chemical agent retainer, a shape and a size of the chemical agent retainer, and a rotational speed of the rotational drive part, are set so that a centrifugal effect of 10 to 150 (G) is obtained in the chemical agent retainer. Therefore, the volatile chemical agent retained in the chemical agent retainer is efficiently vaporized and discharged into the air, and sufficiently diffused. Therefore, even when the chemical agent vaporizing/discharging method having this feature is used in a relatively large space or outdoors, the effect of the volatile chemical agent can be sufficiently exerted.

DESCRIPTION OF EMBODIMENTS

Embodiments relating to a chemical agent vaporizing/discharging device according to the present invention will now be described. This is accompanied by description of a chemical agent vaporizing/discharging method according to the present invention. The present invention is in no way intended to be limited to configurations described in the embodiments below or the accompanying drawings.

A chemical agent vaporizing/discharging device according to the present invention comprises, as basic components, a chemical agent retainer and a rotational drive part. For the sake of convenience, the chemical agent retainer, and a volatile chemical agent retained in the chemical agent retainer, will be first described, and thereafter, a chemical agent vaporizing/discharging device according to the present invention will be described.

(Chemical Agent Retainer)

Figure 1:
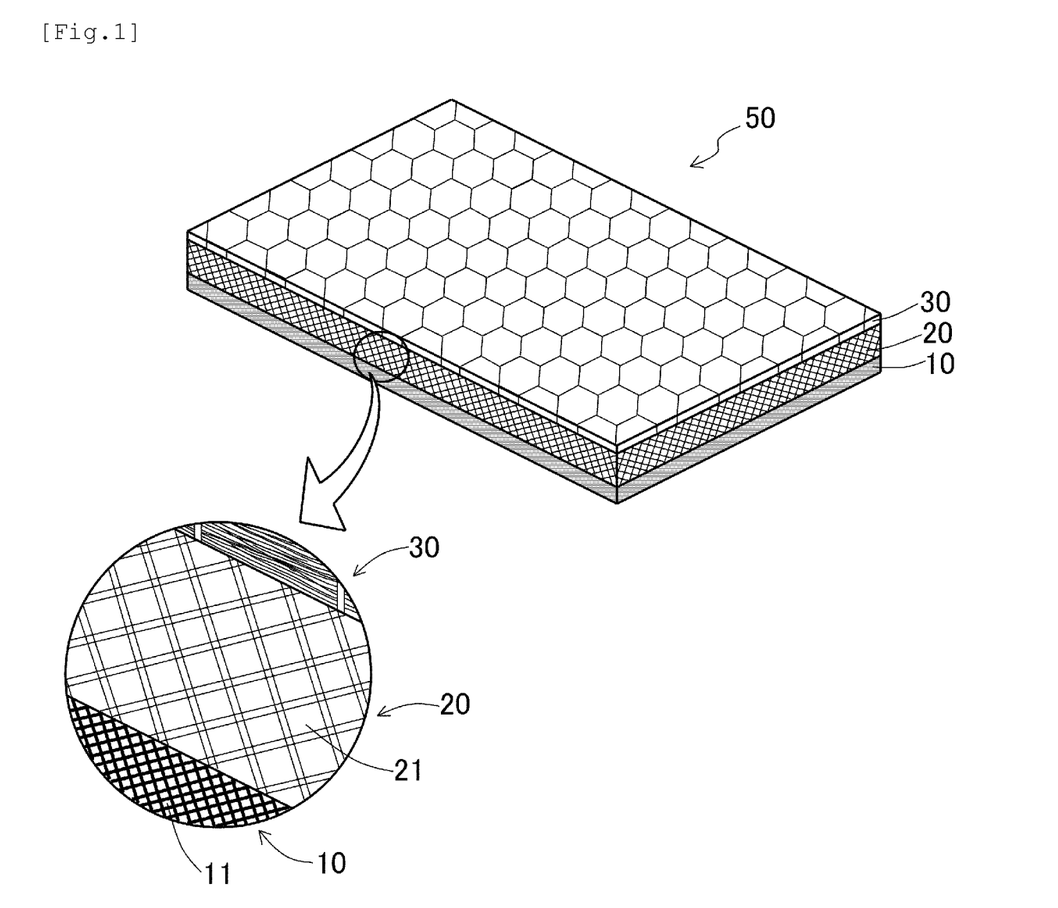
FIG. 1 is a schematic perspective view of a chemical agent retainer which is used in a chemical agent vaporizing/discharging device according to the present invention.

FIG. 1 is a schematic perspective view of a chemical agent retainer 50 which is used in a chemical agent vaporizing/discharging device according to the present invention. In FIG. 1, a larger circle is an enlarged view of a portion of a facet of the chemical agent retainer 50, which is a laminate. The chemical agent retainer 50 comprises a chemical agent retention layer 10 and a gas permeable layer 20, and a form maintenance layer 30 as an optional component. The chemical agent retention layer 10 has interstices 11 which can retain a volatile chemical agent described below. The interstices 11 in the chemical agent retention layer 10 can draw up and retain the volatile chemical agent by capillary action. The gas permeable layer 20 has voids 21 through which air can flow. The voids 21 in the gas permeable layer 20 have a larger size than a size of the interstices 11 in the chemical agent retention layer 10. Therefore, if the volatile chemical agent retained in the interstices 11 of the chemical agent retention layer 10 is moved to the voids 21 of the gas permeable layer 20, the volatile chemical agent can be easily vaporized and discharged into the air.

The chemical agent retention layer 10 and the gas permeable layer 20 preferably include a fibrous structure such as a mesh fiber sheet, woven fabric, nonwoven fabric, knitting, or the like, or alternatively, may include a porous material such as a porous sheet, porous film, or the like. The chemical agent retention layer 10 and the gas permeable layer 20 may be made of either the same or different materials. When the chemical agent retention layer 10 and the gas permeable layer 20 are made of the same material, the chemical agent retention layer 10 having the interstices 11 and the gas permeable layer 20 having the voids 21 which are made of the same material are separately prepared and then joined together to form the chemical agent retainer 50. Alternatively, the chemical agent retention layer 10 and the gas permeable layer 20 may be formed as an integrated fibrous structure or porous structure in which fiber interstices in the fibrous structure or pores in the porous structure are larger in the gas permeable layer 20 than in the chemical agent retention layer 10, in a stepwise or gradient fashion. If the chemical agent retention layer 10 and the gas permeable layer 20 are made of different materials, the chemical agent retention layer 10 is made of a woven fabric, and the gas permeable layer 20 is made of a mesh fiber sheet, and these layers are joined together to provide a fibrous structure, for example. In this case, fibers used in the chemical agent retention layer 10 and the gas permeable layer 20 are selected from materials which can stably vaporize and discharge the volatile chemical agent retained therein, and satisfactorily sustain the state of the vaporization and discharging. Examples of such a material (fiber) for the fibrous structure include: natural fibers, such as cotton, hemp, wool, silk, and the like; semisynthetic fibers, such as rayon and the like; synthetic fibers, such as polyesters (polyethyleneterephthalate, polybutyleneterephthalate, etc.), nylon, acrylic, vinylon, polyethylene, polypropylene, aramid, polyphenylene sulfide, and the like; and inorganic fibers, such as glass fiber, carbon fiber, ceramic fiber, metal fiber, and the like. Of these fibers, polyester and nylon are preferably used. These fibers may be used alone or in combination.

Note that when the chemical agent retention layer 10 and the gas permeable layer 20 are put on top of each other to form the chemical agent retainer 50, the chemical agent retention layer 10 may be provided on one side of the gas permeable layer 20 in the lamination direction as shown FIG. 1, or alternatively, the chemical agent retention layer 10 may be provided on both sides of the gas permeable layer 20. Still alternatively, the chemical agent retention layer 10 and the gas permeable layer 20 may be arranged in alternate layers in this order to form a structure having three or more layers. Furthermore, as long as the chemical agent retention capability or strength of the chemical agent retention layer 10 is not impaired, the chemical agent retention layer 10 may be suitably perforated to have air holes so that the chemical agent vaporizing/discharging performance can be improved.

Incidentally, when the gas permeable layer 20 of the chemical agent retainer 50 has a fibrous structure including a three-dimensional mesh fiber sheet or the like, fiber interstices (the void 21) in the gas permeable layer 20 should be robust in order to ensure good gas permeability of the chemical agent retainer 50. To this end, in the chemical agent retainer 50, as shown in FIG. 1, the form maintenance layer 30 is preferably provided adjacent to the gas permeable layer 20. The form maintenance layer 30 is interwoven with fibers included in the gas permeable layer 20, and thereby functions to maintain the voids 21 of the gas permeable layer 20. Therefore, a sufficient gas permeability of the chemical agent retainer 50 can be ensured. As a result, substantially all the volatile chemical agent retained in the chemical agent retainer 50 can be vaporized and discharged into the air, i.e. can be used up. Note that the gas permeability of the material for the chemical agent retainer 50 is preferably set within the range of 200 to 500 $cm^3/cm^2/sec$ as measured in accordance with Japanese Industrial Standards (JIS L 1096). If the degree of the gas permeability of the material falls within the above range, capillary action is preferably enhanced, so that the volatile chemical agent moves smoothly, leading to efficient vaporization and discharging.

The chemical agent retention layer 10 and the gas permeable layer 20, and the form maintenance layer 30 as an optional component, included in the chemical agent retainer 50, are set to respective suitable thicknesses. The thickness of the chemical agent retention layer 10 is set to 0.05 to 3 mm, preferably 0.2 to 1 mm. If the thickness of the chemical agent retention layer 10 is less than 0.05 mm, the chemical agent retention layer 10 does not have a sufficient capacity to retain the volatile chemical agent, and therefore, has difficulty in sufficiently and sustainably exerting the effect of the volatile chemical agent. If the thickness of the chemical agent retention layer 10 is more than 3 mm, the chemical agent retention layer 10 has an excessive retention capability of the volatile chemical agent, so that a portion of the volatile chemical agent remains in the chemical agent retention layer 10, and therefore, it is difficult to efficiently vaporize and discharge the volatile chemical agent. In addition, the chemical agent retention layer 10 has a large volume, and therefore, it is difficult to form the chemical agent retention layer 10 into various shapes. The gas permeable layer 20 is set to 0.5 to 6 mm, preferably 1 to 5 mm. If the thickness of the gas permeable layer 20 is less than 0.5 mm, the gas permeable layer 20 is excessively humidified with the volatile chemical agent, and an air flow force (stirred air flow) caused by the gas permeable layer is weak, and therefore, it is difficult to efficiently vaporize and discharge the volatile chemical agent. If the thickness of the gas permeable layer 20 is more than 6 mm, the thickness of the chemical agent retention layer 10 should be reduced due to the thickness constraint of the chemical agent retainer 50, and as a result, the chemical agent retention capability of the chemical agent retainer 50 is likely to be impaired, or air flow drag caused by the gas permeable layer 20 is likely to increase, leading to unstable vaporization and discharging of the volatile chemical agent. The form maintenance layer 30 is set to 0.2 to 1 mm. When the thickness of the form maintenance layer 30 falls within this range, the form of the chemical agent retainer 50 can be maintained over a long period of time while the gas permeability of the chemical agent retainer 50 is ensured.

(Volatile Chemical Agent)

The volatile chemical agent retained in the chemical agent retainer 50 may be any chemical agent that has a suitable volatility at room temperature. The amount of the volatile chemical agent retained in the chemical agent retainer 50 is adjustable within the range of 40 to 2000 mg, depending on conditions such as an application thereof, a period of time during which the activity should be sustained, and the like. Examples of a volatile chemical agent which can be used in the present invention include volatile pyrethroid compounds, insecticides, acaricides, repellents, antimicrobials, insect repellent aroma chemicals, deodorants, and the like. Of these agents, volatile pyrethroid compounds are a volatile chemical agent having an excellent insect repelling effect and insect killing effect, and therefore, are preferably used. In particular, a pyrethroid compound having a vapor pressure of $2 \times 10^{-4}$ to $1 \times 10^{-2}$ mmHg at 30° C. has a good balance between volatility and sustainability, and therefore, is more preferably used. Examples of a useful volatile pyrethroid compound include 2,3,5,6-tetrafluorobenzyl 2,2-dimethyl-3-(2,2-dichlorovinyl)cyclopropane carboxylate (transfluthrin), 4-methyl-2,3,5,6-tetrafluorobenzyl 2,2-dimethyl-3-(1-propenyl)cyclopropane carboxylate (profluthrin), 4-methoxymethyl-2,3,5,6-tetrafluorobenzyl 2,2-dimethyl-3-(1-propenyl) cyclopropane carboxylate (metofluthrin), 4-methoxymethyl-2,3,5,6-tetrafluorobenzyl 2,2,3,3-tetramethylcyclopropane carboxylate, 4-propargyl-2,3,5,6-tetrafluorobenzyl 2,2,3,3-tetramethylcyclopropane carboxylate, empenthrin, and the like. Some of these pyrethroid compounds have various isomers. In this case, one of the isomers may be used alone, or a mixture containing some or all of the isomers at any suitable ratio may be used. Two or more of the above pyrethroid compounds may be suitably selected and their volatilities may be adjusted to provide a formulation which can be used for a long period of time.

Examples of insecticides as a volatile chemical agent other than the above pyrethroid compounds, include neonicotinoid insecticidal ingredients, such as dinotefuran and the like, organic phosphorus insecticidal ingredients, such as fenitrothion and the like, and carbamate insecticidal ingredients, such as propoxur and the like. Examples of acaricides include 5-chloro-2-trifluoromethanesulfonamide methyl benzoate, phenyl salicylate, 3-iodo-2-propynylbutyl carbamate, and the like. Examples of repellents (repelling ingredients) include DEET, dimethyl phthalate, 2-ethyl-1,3-hexanediol, and the like. Examples of antimicrobials (antimicrobial ingredients) include hinokitiol, tetrahydrolinalool, eugenol, allyl isothiocyanate, and the like. Examples of insect repellent aroma chemicals include citronella oil, orange oil, lemon oil, lime oil, yuzu oil, lavender oil, peppermint oil, *eucalyptus* oil, jasmine oil, cypress oil, green tea essential oil, limonene, α-pinene, citronellal, terpineol, linalool, geraniol, phenylethyl alcohol, amylcinnamic aldehyde, cuminaldehyde, benzyl acetate, and the like. In addition to deodorants, it is useful to blend a leaf alcohol or leaf aldehyde called "fragrance of green."

The volatile chemical agent may be used directly, or alternatively, may be diluted with various solvents, or may be blended with various additives. Examples of such a solvent include hydrocarbon solvents, such as n-paraffin, isoparaffin, and the like, glycols having 3 to 6 carbon atoms, such as propylene glycol, 1,3-butylene glycol, 1,4-butylene glycol, diethylene glycol, dipropylene glycol, hexylene glycol, and the like, glycol ethers, ketone solvents, ester solvents, and the like. The volatile chemical agent is suitably diluted using these solvents, and the resultant dilution is retained in the chemical agent retainer 50. Examples of the additives include stabilizers, such as BHT, BHA, 2,2'-methylene bis(4-ethyl-6-t-butylphenol), 2,2'-methylene bis(4-methyl-6-t-butylphenol), 4,4'-methylene bis(2-methyl-6-t-butylphenol), 3,5-di-t-butyl-4-hydroxyanisole, mercaptobenzimidazole, and the like. Various ingredients may be optionally added, such as a UV absorber, UV scattering agent, brightening agent, anti-inflammatory agent, antiperspirant, moisturizer, surfactant, dispersant, aroma chemical, and the like.

(Chemical Agent Vaporizing/Discharging Device)

Next, a chemical agent vaporizing/discharging device according to the present invention which comprises the above chemical agent retainer will be described. The chemical agent vaporizing/discharging device of the present invention is used to vaporize and discharge a volatile chemical agent such as an insecticide, repellent, or the like, into the air in order to control flying insect pests, such as mosquitoes, nonbiting midges, small flies, and the like, and creeping insect pests, such as cockroaches, ants, centipedes, spiders, and the like. Two representative examples of the chemical agent vaporizing/discharging device of the present invention will now be described.

First Embodiment

Figure 2:
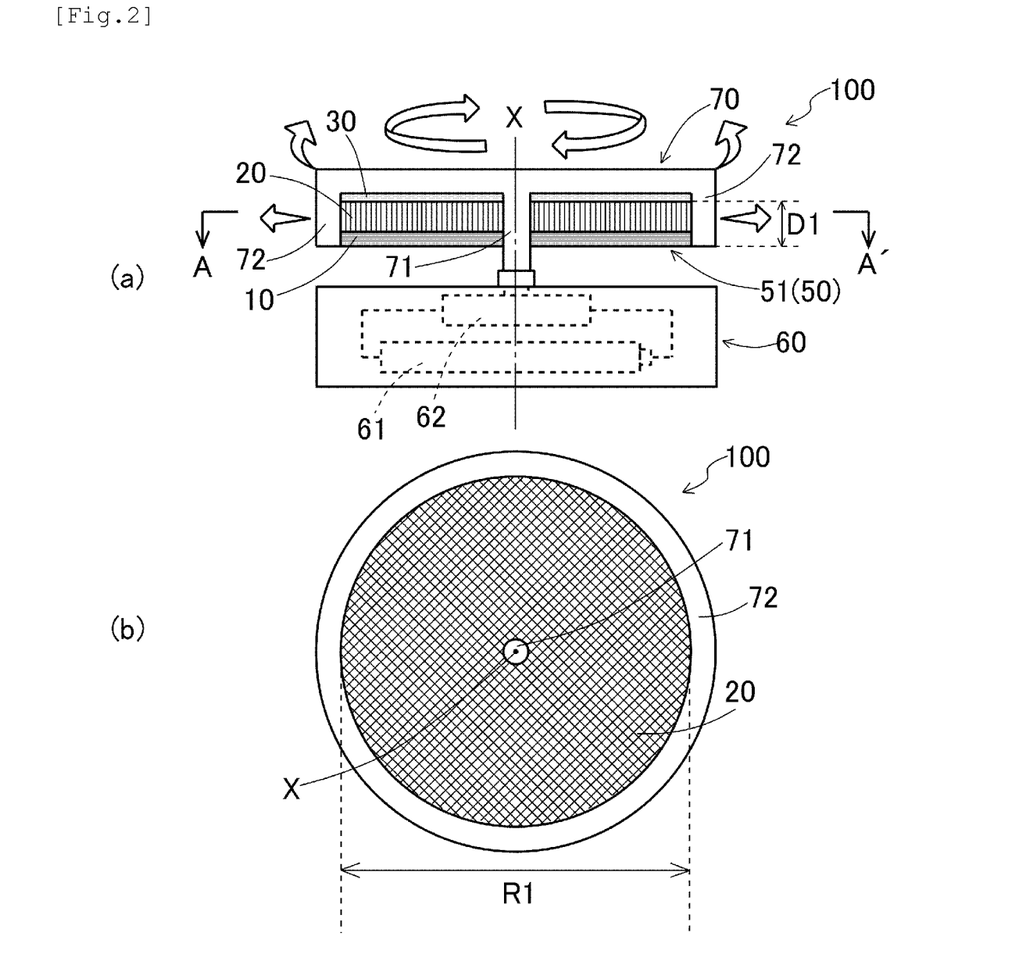
FIG. 2 is a schematic diagram of a configuration of a chemical agent vaporizing/discharging device according to a first embodiment of the present invention.

FIG. 2 is a schematic diagram of a configuration of a chemical agent vaporizing/discharging device 100 according to a first embodiment of the present invention. FIG. 2(a) is a vertical cross-sectional view of the chemical agent vaporizing/discharging device 100. FIG. 2(b) is a horizontal cross-sectional view of the chemical agent vaporizing/discharging device 100 taken along line A-A' of FIG. 2(a). The chemical agent vaporizing/discharging device 100 comprises, as basic components, a chemical agent retainer 51 and a rotational drive part 60. The chemical agent retainer 51 is a laminate of a chemical agent retention layer 10 and a gas permeable layer 20. A form maintenance layer 30 is provided adjacent to the gas permeable layer 20. In the chemical agent vaporizing/discharging device 100 of this embodiment, the chemical agent retainer 51 is formed in the shape of a disc as shown in FIG. 2(*b*). Specifically, the chemical agent retainer 50 which is a laminate sheet of the chemical agent retention layer 10, the gas permeable layer 20, and the form maintenance layer 30 shown in FIG. 1 is die-cut into a circular shape. In this case, the size of the chemical agent retainer 51 is set as follows: the diameter R1 of the chemical agent retainer 51 is about 4 to 8 cm; and the thickness D1 of the laminate of the chemical agent retention layer 10 and the gas permeable layer 20 is about 1 to 7 mm. Such a disc shape allows a reduction in the thickness of the chemical agent retainer 51, and therefore, excellent portability can be imparted to the chemical agent vaporizing/discharging device 100.

The disc-shaped chemical agent retainer 51 is housed in a rotating cartridge 70 in use. The rotating cartridge 70 comprises a shaft 71 and a case 72. The chemical agent retainer 51 is fixed to the shaft 71 with the shaft 71 penetrating through a center of the chemical agent retainer 51. The case 72 of the rotating cartridge 70 is provided with a suitable opening (not shown) so that a volatile chemical agent is efficiently vaporized and discharged from the chemical agent retainer 51. The shaft 71 of the rotating cartridge 70 is coupled to the rotational drive part 60. The rotational drive part 60, which includes a power supply 61 and a drive motor 62, can rotate the rotating cartridge 70 housing the chemical agent retainer 51 at a predetermined rotational speed. Thus, when the chemical agent retainer 51 housed in the rotating cartridge 70 is rotated by the rotational drive part 60, the chemical agent retainer 51 is inhibited from being deformed by a centrifugal force, and therefore, variations in a centrifugal effect (described below) during rotation of the chemical agent retainer 51 can be reduced. The power supply 61 of the rotational drive part 60 may be either a direct current power supply or an alternating current power supply. When the chemical agent vaporizing/discharging device 100 is carried, a battery is preferably used, such as an alkaline battery, zinc-carbon battery, rechargeable battery, solar battery, or the like. The capacity of the battery may be suitably selected according to usage or dosage. For example, when the chemical agent vaporizing/discharging device 100 is used as a portable or indoor vaporizing/discharging device, a C, AA, or AAA battery is preferably used. When the chemical agent vaporizing/discharging device 100 is used as a large-scale vaporizing/discharging device for a large space, a plurality of D or C batteries are preferably used. The drive motor 62 may be any commonly used motor, such as, for example, a brushed motor or brushless motor. In particular, brushless motors are excellently durable and usable, and therefore, are suitably used as the drive motor 62 of the chemical agent vaporizing/discharging device 100. The speed of revolution of the drive motor 62 (i.e., the speed of revolution of the chemical agent retainer 51) is set to 500 to 2000 rpm, preferably 700 to 1600 rpm. If the speed of revolution is less than 500 rpm, the chemical agent vaporizing/discharging effect is less likely to be sufficient. If the speed of revolution is more than 2000 rpm, then when a battery is used as the power supply 61, charge is more quickly consumed, and therefore, the chemical agent vaporizing/discharging device 100 cannot perform long-term operation. The rotational drive part 60 may be provided with an on-off switch, a pilot light or the like for indicating the end of operation, or the like. If a pilot light or the like is provided, the surface temperature of the rotational drive part 60 is slightly increased due to heat generation, and therefore, by utilizing the heat, the vaporization of the volatile chemical agent retained in the chemical agent retainer 51 can be enhanced.

When the rotational drive part 60 is driven, the chemical agent retainer 51 and the rotating cartridge 70 are rotated, as an integrated structure, around the shaft center (axis of rotation) X of the shaft 71. At this time, a centrifugal force is exerted on the chemical agent retainer 51 due to the rotation, which is accompanied by a stirred air flow occurring around the chemical agent retainer 51 as indicated by arrows in FIG. 2(*a*). As a result, the volatile chemical agent retained in the chemical agent retention layer 10 is vaporized and discharged from the gas permeable layer 20 into the air, and is further diffused, so that an insect repelling effect and an insect killing effect are exerted around the chemical agent vaporizing/discharging device 100.

Second Embodiment

FIG. 3 is a schematic diagram of a configuration of a chemical agent vaporizing/discharging device 200 according to a second embodiment of the present invention. FIG. 3(*a*) is a vertical cross-sectional view of the chemical agent vaporizing/discharging device 200. FIG. 3(*b*) is a horizontal cross-sectional view of the chemical agent vaporizing/discharging device 200 taken along line B-B' of FIG. 3(*a*). The chemical agent vaporizing/discharging device 200 comprises, as basic components, a chemical agent retainer 52 and a rotational drive part 60, as with the chemical agent vaporizing/discharging device 100 of the first embodiment. The chemical agent retainer 52 is a laminate of a chemical agent retention layer 10 and a gas permeable layer 20. A form maintenance layer 30 is provided adjacent to the gas permeable layer 20. In the chemical agent vaporizing/discharging device 200 of this embodiment, the chemical agent retainer 52 is formed in the shape of a hollow cylinder as shown in FIG. 3(*b*). Specifically, to provide this form, the sheet-shaped chemical agent retainer 50 of FIG. 1, which is a laminate of the chemical agent retention layer 10, the gas permeable layer 20, and the form maintenance layer 30, is rolled into a cylindrical shape with the chemical agent retention layer 10 facing inward. In this case, the size of the chemical agent retainer 52 is set as follows: the inner diameter R2 of the chemical agent retainer 52 is about 6 to 10 cm; the thickness D2 of the laminate of the chemical agent retention layer 10 and the gas permeable layer 20 is about 1 to 7 mm; and the height T1 of the chemical agent retainer 52 is 3 to 10 cm, respectively. In such a hollow cylindrical chemical agent retainer 52, all points along the length direction on the chemical agent retention layer 10 are equidistant from the center axis (axis of rotation described below), and therefore, substantially the same centrifugal effect (described below) is exerted on the volatile chemical agent at every point on the chemical agent retention layer 10. As a result, the chemical agent vaporizing/discharging effect can be exerted substantially uniformly all the way around the chemical agent retainer 52.

The hollow cylindrical chemical agent retainer 52 is housed in a rotating cartridge 70 in use. The rotating cartridge 70 comprises a shaft 71, a case 72, and a holding piece 73. The chemical agent retainer 52 is inserted and fixed between the case 72 and the holding piece 73. The case 72 of the rotating cartridge 70 is provided with a suitable opening (not shown) in order to efficiently vaporize and discharge the volatile chemical agent from the chemical agent retainer 52. The shaft 71 of the rotating cartridge 70 is coupled to the rotational drive part 60, which includes a power supply 61 and a drive motor 62. The rotational drive part 60 has a similar configuration to that of the first embodiment, which will not be described in detail.

Figure 3:
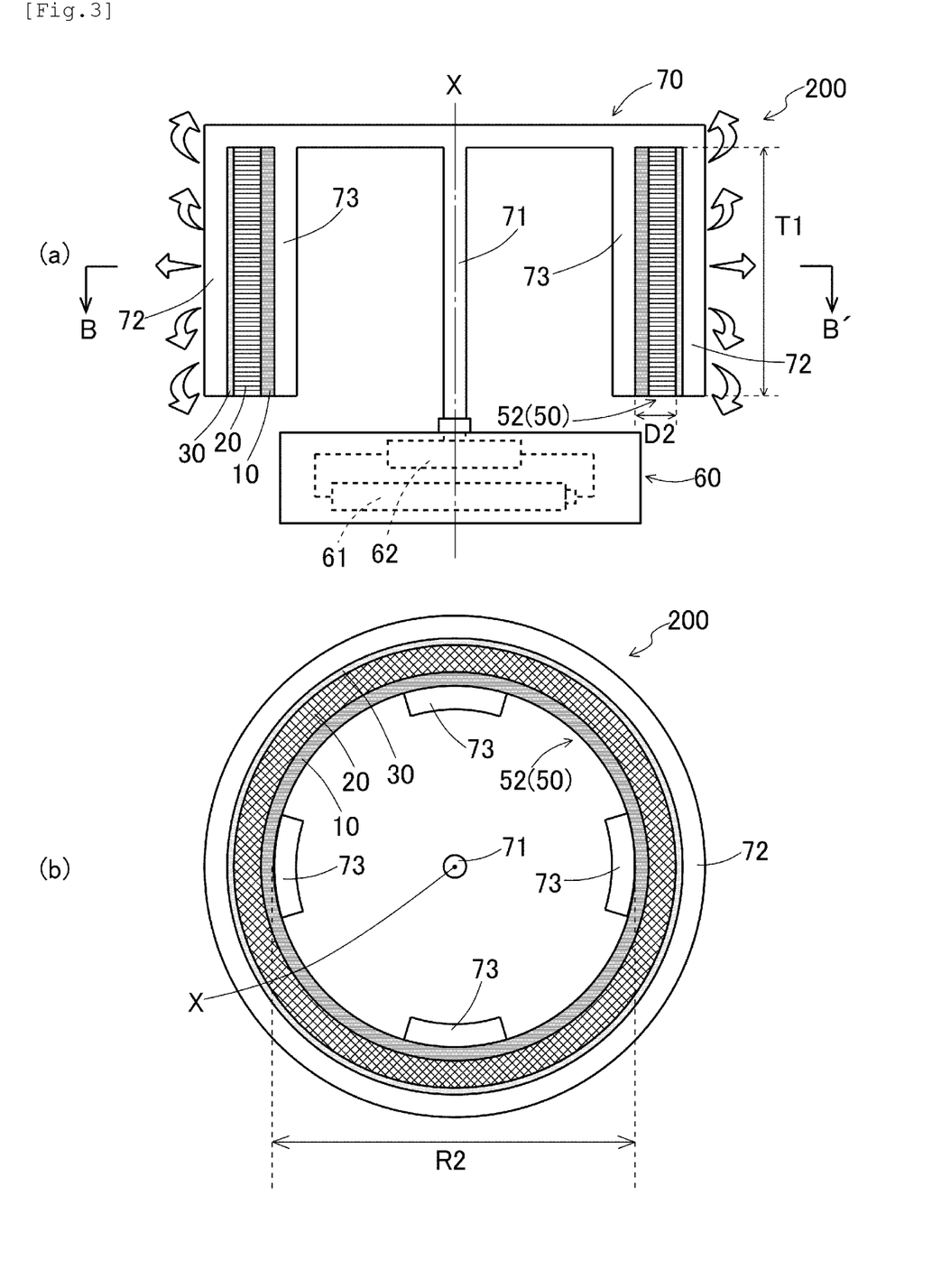
FIG. 3 is a schematic diagram of a configuration of a chemical agent vaporizing/discharging device according to a second embodiment of the present invention.

When the rotational drive part 60 is driven, the chemical agent retainer 52 and the rotating cartridge 70 are rotated, as an integrated structure, around the shaft center (axis of rotation) X of the shaft 71. At this time, a centrifugal force is exerted on the chemical agent retainer 52 due to the rotation, which is accompanied by a stirred air flow occurring around the chemical agent retainer 52 as indicated by arrows in FIG. 3($a$). As a result, the volatile chemical agent retained in the chemical agent retention layer 10 is vaporized and discharged from the gas permeable layer 20 into the air, and is further diffused, so that an insect repelling effect and an insect killing effect are exerted around the chemical agent vaporizing/discharging device 200.

(Centrifugal Effect in Chemical Agent Vaporizing/Discharging Device)

In the chemical agent vaporizing/discharging device 100 of the first embodiment and the chemical agent vaporizing/discharging device 200 of the second embodiment, settings are made to obtain a suitable centrifugal effect during rotation of the chemical agent retainer 50 (51, 52). Here, the centrifugal effect (G) is an index which indicates the strength of a centrifugal force exerted on a rotating object, and has a numerical value ($G=m/sec^2$) represented by:

$$\text{Centrifugal effect } (G)=R\times N^2/894 \qquad \text{(I)}$$

(R: the radius of rotation (m), N: the speed of revolution (rpm))

The present inventors have found that when the shape and size of the chemical agent retainer 50 (51, 52) are set, and furthermore, the rotational speed of the rotational drive part 60 is adjusted so that a centrifugal effect of 10 to 150 (G) is obtained during rotation of the chemical agent retainer 50 (51, 52), the volatile chemical agent can be efficiently vaporized and discharged from the chemical agent retainer 50 (51, 52), and sufficiently diffused. If the centrifugal effect is less than 10 (G), the vaporizing/discharging performance of the chemical agent vaporizing/discharging device 100, 200 is less likely to be sufficient, and therefore, the insect repelling effect and insect killing effect of the volatile chemical agent are less likely to be sufficient. If the centrifugal effect is more than 150 (G), the volatile chemical agent retained in the chemical agent retainer 50 (51, 52) is likely to be scattered to surroundings, and therefore, the insect repelling effect and insect killing effect are less likely to be sufficient. Furthermore, the volatile chemical agent in liquid form may be scattered so that surroundings become dirty. When the chemical agent vaporizing/discharging device 100, 200 is used to carry out the chemical agent vaporizing/discharging method of the present invention, then if the rotational speed of the chemical agent retainer 50 (51, 52) is adjusted so that a centrifugal effect of 10 to 150 (G) is obtained (rotation adjustment step), the volatile chemical agent retained in the chemical agent retainer 50 (51, 52) can be efficiently vaporized and discharged into the air, and sufficiently diffused. Therefore, even when the chemical agent vaporizing/discharging device 100, 200 is used in a relatively large space or outdoors, the insect repelling effect and insect killing effect can be sufficiently exerted.

As to the vaporizing/discharging performance of the chemical agent vaporizing/discharging device 100, 200, the voids 21 of the gas permeable layer 20 are set to a size larger than a size of the interstices 11 of the chemical agent retention layer 10. Therefore, a stirred air flow occurring due to rotation of the chemical agent retainer 50 (51, 52) may affect vaporization and discharging of the volatile chemical agent. The present inventors have further extensively studied to find that if the thickness ratio of the chemical agent retention layer 10 and the gas permeable layer 20 included in the chemical agent retainer 50 (51, 52) is set to a suitable value within the range which allows the above centrifugal effect (G), the chemical agent vaporizing/discharging device 100, 200 can efficiently exert the vaporizing/discharging performance. Here, the thickness ratio (P) $\{P=A/B\}$ of the gas permeable layer 20 and the chemical agent retention layer 10 is preferably set to more than 1.5 and not more than 50, where A represents the thickness of the gas permeable layer 20, and B represents the thickness of the chemical agent retention layer 10. If the thickness ratio (P) is not more than 1.5, the thickness (A) of the gas permeable layer 20 is insufficient with respect to the thickness (B) of the chemical agent retention layer 10, and therefore, the volatile chemical agent retained in the chemical agent retention layer 10 is less likely to be stably vaporized and discharged. Furthermore, a stirred air flow caused by the gas permeable layer 20 becomes weak, and therefore, the efficiency of vaporization and discharging of the volatile chemical agent is reduced. Meanwhile, if the thickness ratio (P) is more than 50, the thickness (A) of the gas permeable layer 20 is excessively large with respect to the thickness (B) of the chemical agent retention layer 10, so that most of the volatile chemical agent retained in the chemical agent retention layer 10 is quickly vaporized and discharged, and therefore, the sustained effect of the volatile chemical agent is less likely to be obtained. When the chemical agent retainer 50 (51, 52) is housed in the rotating cartridge 70, there is a constraint on the sum of the thicknesses of the chemical agent retention layer 10 and the gas permeable layer 20, and therefore, the thickness of the chemical agent retention layer 10 is relatively small. As a result, the amount of the volatile chemical agent retained is reduced, and therefore, the effect of the volatile chemical agent is less likely to be exerted for a long period of time.

Furthermore, the present inventors have closely studied a relationship between the centrifugal effect (G) and the thickness ratio (P) to find that if a centrifugal vaporizing/discharging index (T) is set within a suitable range, taking into consideration factors such as a rotational load and the like, where the centrifugal vaporizing/discharging index (T) is a value (G/P) obtained by dividing the centrifugal effect (G) by the thickness ratio (P), the chemical agent vaporizing/discharging device 100, 200 can more efficiently exert the vaporizing/discharging performance. The present invention is effective when the rotational speed (i.e., the speed of revolution of the rotational drive part 60) of the chemical agent retainer 50 (51, 52) is set so that the centrifugal vaporizing/discharging index (T) is more than 1.1 and less than 22. In this case, the volatile chemical agent retained in the chemical agent retainer 50 (51, 52) is more efficiently vaporized and discharged, and sufficiently diffused in the air. Therefore, even when the chemical agent vaporizing/discharging device 100, 200 is used in a larger space or outdoors, the insect repelling effect and insect killing effect can be reliably exerted.

Note that, in the chemical agent vaporizing/discharging device 200 of the second embodiment, the chemical agent retainer 52 has a hollow cylindrical shape, and therefore, compared to the disc-shaped chemical agent retainer 51 of the first embodiment, has a larger size and tends to receive a greater rotational load. Meanwhile, the chemical agent retention layer 10 can have a larger surface area in the hollow cylindrical chemical agent retainer 52 than in the disc-shaped chemical agent retainer 51. Therefore, in the second embodiment, the thickness of the chemical agent retention layer 10 may be reduced so that an increase in rotational load is canceled.

EXAMPLES

In order to verify the insect repelling effect and the insect killing effect when the chemical agent vaporizing/discharging device of the present invention is used, outdoor effect verification tests (Examples 1, 2, and 3) and indoor effect verification tests (Examples 4 and 5) were conducted.

Example 1

A chemical agent retention layer including polyester fibers (thickness: 0.3 mm) and a gas permeable layer including polyester fibers (thickness: 1.6 mm) were joined together into a laminate using twisted polyester fibers, and a form maintenance layer (thickness: 0.2 mm) including polyester fibers was provided adjacent to and on top of the gas permeable layer, to form a disc-shaped chemical agent retainer (thickness: 2.1 mm, outer diameter: 4.5 cm). In the chemical agent retainer, the thickness ratio (P) of the gas permeable layer and the chemical agent retention layer is 5.3. Next, the chemical agent retainer was housed in a rotating cartridge made of polycarbonate (thickness: 8 mm, outer diameter: 5.2 cm). A chemical liquid obtained by dissolving 40 mg of metofluthrin in 0.07 mL of kerosene was dropped, as a volatile chemical agent, throughout the chemical agent retainer, so that metofluthrin was retained in the chemical agent retainer. Thereafter, the rotating cartridge was coupled to the rotational drive part. A chemical agent vaporizing/discharging device of Example 1 was thus configured.

In the chemical agent vaporizing/discharging device of Example 1, when the rotational drive part was rotated at 1200 rpm (in this case, the chemical agent retainer was also rotated at 1200 rpm), the centrifugal effect (G) exerted on the chemical agent retainer was 36.2 (G), and the centrifugal vaporizing/discharging index (T) obtained by dividing the centrifugal effect (G) by the thickness ratio (P) was 6.8. When the chemical agent vaporizing/discharging device was attached to the waist of a subject, and was carried by the subject outdoors for a total of 120 hours while the rotational drive part was rotating, the subject was not annoyed by unpleasant insect pests such as mosquitoes and the like during the test. Thus, for the chemical agent vaporizing/discharging device of Example 1, an excellent insect repelling effect caused by vaporization and discharging of the volatile chemical agent was verified.

Example 2

Two of the disc-shaped chemical agent retainers formed in Example 1 were put on top of each other, and were housed in the same polycarbonate rotating cartridge as that of Example 1. A chemical liquid obtained by dissolving 60 mg of metofluthrin in 0.08 mL of kerosene was dropped, as a volatile chemical agent, throughout the chemical agent retainer, so that metofluthrin was retained in the chemical agent retainer. Thereafter, the rotating cartridge was coupled to the rotational drive part. A chemical agent vaporizing/discharging device of Example 2 was thus configured.

The chemical agent vaporizing/discharging device of Example 2 was operated in a manner similar to that in Example 1. As a result, the insect repelling effect was effective over 240 hours.

Example 3

A plate-like three-dimensional fiber structure including polyester fibers (thickness: 4.5 mm) was directly used as a chemical agent retainer. Therefore, in the chemical agent retainer, a chemical agent retention layer (thickness: 0.3 mm), a gas permeable layer (thickness: 3.9 mm), and a form maintenance layer (thickness: 0.3 mm) were integrally formed. In the chemical agent retainer, the thickness ratio (P) of the gas permeable layer and the chemical agent retention layer was 13. Next, a chemical liquid obtained by dissolving 1.2 g of transfluthrin in 1.2 mL of kerosene was dropped, as a volatile chemical agent, throughout the chemical agent retainer, so that transfluthrin was retained in the chemical agent retainer. Thereafter, the chemical agent retainer was rolled into a cylinder so that a hollow cylindrical shape was formed. The resultant structure was housed in a polycarbonate rotating cartridge (diameter: 8 cm, height: 5 cm). Thereafter, the rotating cartridge was coupled to the rotational drive part. A chemical agent vaporizing/discharging device of Example 3 was thus configured.

In the chemical agent vaporizing/discharging device of Example 3, when the rotational drive part was rotated at 1000 rpm (in this case, the chemical agent retainer was also rotated at 1000 rpm), the centrifugal effect (G) exerted on the chemical agent retainer was 44.7 (G), and the centrifugal vaporizing/discharging index (T) obtained by dividing the centrifugal effect (G) by the thickness ratio (P) was 3.4. The chemical agent vaporizing/discharging device was placed outdoors while the rotational drive part was rotating, and was used for a total of 960 hours. Substantially no flying insect pests such as mosquitoes and the like entered the range of about 5 m around the chemical agent vaporizing/discharging device during the test. Thus, for the chemical agent vaporizing/discharging device of Example 3, an excellent insect repelling effect caused by vaporization and discharging of the volatile chemical agent was verified.

Example 4

A disc-shaped chemical agent retainer retaining a volatile chemical agent was formed using a procedure similar to that of Example 1, and was housed in a polycarbonate rotating cartridge similar to that of Example 1. The rotating cartridge was coupled to a rotational drive part. A chemical agent vaporizing/discharging device of Example 4 was thus configured. Note that the chemical agent vaporizing/discharging device of Example 4 was designed for 240-hour use, and therefore, the thickness of the disc-shaped chemical agent retainer was about two times as large as the thickness of Example 1, and the amount of metofluthrin as the volatile chemical agent was 60 mg per chemical agent retainer. In Example 4, a plurality of chemical agent retainers having different diameters (R1) and different thickness ratios (P) of the gas permeable layer and the chemical agent retention layer were prepared. By changing the speed of revolution (N), centrifugal effect (G), and centrifugal vaporizing/discharging index (T) of the chemical agent retainer, differences in the effect of the volatile chemical agent were studied (test nos. 1 to 41 in Table 1). Specifically, the chemical agent vaporizing/discharging devices of test nos. 1 to 41 were each placed at a center of a room having an area of 6 Jyos (25 m$^3$) in which 100 female adults of *Culex pipiens* were released, and an insect killing effect caused by the volatile chemical agent was verified. The insect killing effect was evaluated using KT50. A case where the time it took to knock down 50% of the *Culex pipiens* mosquitoes was not less than 5 min and less than 30 min is indicated by a double circle. A case where such a time was not less than 30 min and less than 60 min is indicated by a single circle. A case where such a time was not less than 60 min and less than 90 min is indicated by a triangle. A case where such a time was not less than 90 min is indicated by a cross.

centrifugal vaporizing/discharging index (T) is set to a value of more than 1.1 and less than 22, a more excellent insect killing effect is obtained. In contrast to this, if the thickness (B) of the chemical agent retention layer is small, and the thickness ratio (P) is more than 50, as in test nos. 18 and 23, the chemical agent retention capability of the chemical agent retainer is insufficient, and therefore, the exertion of the insect killing effect is likely to be impaired. Furthermore, if the thickness (A) of the gas permeable layer is small, and the thickness ratio (P) is not more than 1.5, as in test nos. 22 and 27, a stirred air flow caused by the gas permeable layer is weak, and therefore, the efficiency of vaporization and discharging of the volatile chemical agent tends to be reduced.

Example 5

A hollow cylindrical chemical agent retainer retaining a volatile chemical agent was formed using a procedure

TABLE 1

| Test no. | Diameter (R1) (cm) | Speed of revolution (N) (rpm) | Centrifugal effect (G) (m/s$^2$) | Thickness ratio (P): {gas permeable layer (A)/ chemical agent retention layer (B)} | Centrifugal vaporizing/discharging index (T): (G/P) | Insect killing effect |
|---|---|---|---|---|---|---|
| 1 | 4.0 | 500 | 5.6 | | | X |
| 2 | | 700 | 11.0 | 19 (3.8 mm/0.2 mm) | 0.57 | Δ |
| 3 | | | | 7 (3.5 mm/0.5 mm) | 1.57 | ○ |
| 4 | | | | 3 (3.0 mm/1.0 mm) | 3.67 | ○ |
| 5 | | 1200 | 32.2 | 19 (3.8 mm/0.2 mm) | 1.69 | ○ |
| 6 | | | | 7 (3.5 mm/0.5 mm) | 4.60 | ⊚ |
| 7 | | | | 3 (3.0 mm/1.0 mm) | 10.7 | ⊚ |
| 8 | | 1600 | 57.3 | 19 (3.8 mm/0.2 mm) | 3.02 | ⊚ |
| 9 | | | | 7 (3.5 mm/0.5 mm) | 8.19 | ⊚ |
| 10 | | | | 3 (3.0 mm/1.0 mm) | 19.1 | ○ |
| 11 | | 2000 | 89.5 | 19 (3.8 mm/0.2 mm) | 4.71 | ○ |
| 12 | | | | 7 (3.5 mm/0.5 mm) | 12.8 | ○ |
| 13 | | | | 3 (3.0 mm/1.0 mm) | 29.8 | Δ |
| 14 | 6.0 | 500 | 8.4 | | | X |
| 15 | | 700 | 16.4 | 19 (3.8 mm/0.2 mm) | 0.86 | Δ |
| 16 | | | | 7 (3.5 mm/0.5 mm) | 2.34 | ○ |
| 17 | | | | 3 (3.0 mm/1.0 mm) | 5.47 | ⊚ |
| 18 | | 1200 | 48.3 | 79 (3.95 mm/0.05 mm) | 0.62 | — |
| 19 | | | | 19 (3.8 mm/0.2 mm) | 2.54 | ⊚ |
| 20 | | | | 7 (3.5 mm/0.5 mm) | 6.90 | ⊚ |
| 21 | | | | 3 (3.0 mm/1.0 mm) | 16.1 | ○ |
| 22 | | | | 1 (2.0 mm/2.0 mm) | 48.3 | Δ |
| 23 | | 1600 | 85.9 | 79 (3.95 mm/0.05 mm) | 1.09 | — |
| 24 | | | | 19 (3.8 mm/0.2 mm) | 4.52 | ⊚ |
| 25 | | | | 7 (3.5 mm/0.5 mm) | 12.3 | ⊚ |
| 26 | | | | 3 (3.0 mm/1.0 mm) | 28.6 | Δ |
| 27 | | | | 1 (2.0 mm/2.0 mm) | 85.9 | Δ |
| 28 | | 2000 | 134.2 | | | Δ |
| 29 | 8.0 | 500 | 11.2 | 19 (3.8 mm/0.2 mm) | 0.59 | Δ |
| 30 | | | | 7 (3.5 mm/0.5 mm) | 1.60 | ○ |
| 31 | | | | 3 (3.0 mm/1.0 mm) | 3.73 | ○ |
| 32 | | 700 | 21.9 | 19 (3.8 mm/0.2 mm) | 1.15 | ○ |
| 33 | | | | 7 (3.5 mm/0.5 mm) | 3.13 | ⊚ |
| 34 | | | | 3 (3.0 mm/1.0 mm) | 7.30 | ⊚ |
| 35 | | 1200 | 64.4 | 19 (3.8 mm/0.2 mm) | 3.39 | ⊚ |
| 36 | | | | 7 (3.5 mm/0.5 mm) | 9.20 | ⊚ |
| 37 | | | | 3 (3.0 mm/1.0 mm) | 21.5 | ○ |
| 38 | | 1600 | 114.5 | 19 (3.8 mm/0.2 mm) | 6.03 | ⊚ |
| 39 | | | | 7 (3.5 mm/0.5 mm) | 16.4 | ⊚ |
| 40 | | | | 3 (3.0 mm/1.0 mm) | 38.2 | Δ |
| 41 | | 2000 | 179.0 | | | X |

As can be seen from Table 1, if the diameter (R1) and the speed of revolution (N) of the chemical agent retainer are set so that the centrifugal effect (G) exerted on the chemical agent retainer falls within the range of 10 to 150 (m/s$^2$), at least a predetermined level of insect killing effect is obtained. Furthermore, if the thickness ratio (P) is set to a value of more than 1.5 and not more than 50, and the similar to that of Example 3, and was housed in a polycarbonate rotating cartridge similar to that of Example 3. The rotating cartridge was coupled to a rotational drive part. A chemical agent vaporizing/discharging device of Example 5 was thus configured. In Example 5, a plurality of chemical agent retainers having different inner diameter (R2) and different thickness ratios (P) of the gas permeable layer and the chemical agent retention layer were prepared. By changing the speed of revolution (N), centrifugal effect (G), and centrifugal vaporizing/discharging index (T) of the chemical agent retainer, differences in the effect of the volatile chemical agent were studied (test nos. 42 to 81 in Table 2). A test method for the effect verification test and a method for evaluating the insect killing effect were similar to those of Example 4, except that the test was conducted in a room having an area of 25 Jyos (105 m$^3$).

weak, and therefore, the efficiency of vaporization and discharging of the volatile chemical agent tends to be reduced.

INDUSTRIAL APPLICABILITY

The chemical agent vaporizing/discharging device and method of the present invention are used in order to repel or kill flying insect pests such as mosquitoes, black flies,

TABLE 2

| Test no. | Diameter (R2) (cm) | Speed of revolution(N) (rpm) | Centrifugal effect (G) (m/s$^2$) | Thickness ratio (P): {gas permeable layer (A)/ chemical agent retention layer (B)} | Centrifugal vaporizing/discharging index (T): (G/P) | Insect killing effect |
|---|---|---|---|---|---|---|
| 42 | 6.0 | 500 | 8.4 | | | X |
| 43 | | 700 | 16.4 | 24 (4.8 mm/0.2 mm) | 0.68 | Δ |
| 44 | | | | 9 (4.5 mm/0.5 mm) | 1.82 | ○ |
| 45 | | | | 4 (4.0 mm/1.0 mm) | 4.10 | ○ |
| 46 | | 1000 | 33.6 | 24 (4.8 mm/0.2 mm) | 1.40 | ○ |
| 47 | | | | 9 (4.5 mm/0.5 mm) | 3.73 | ◎ |
| 48 | | | | 4 (4.0 mm/1.0 mm) | 8.40 | ◎ |
| 49 | | 1400 | 65.8 | 24 (4.8 mm/0.2 mm) | 2.74 | ◎ |
| 50 | | | | 9 (4.5 mm/0.5 mm) | 7.31 | ◎ |
| 51 | | | | 4 (4.0 mm/1.0 mm) | 16.5 | ○ |
| 52 | | 1800 | 108.7 | 24 (4.8 mm/0.2 mm) | 4.53 | ◎ |
| 53 | | | | 9 (4.5 mm/0.5 mm) | 12.1 | ◎ |
| 54 | | | | 4 (4.0 mm/1.0 mm) | 27.2 | Δ |
| 55 | 8.0 | 500 | 11.2 | | | Δ |
| 56 | | 700 | 21.9 | 24 (4.8 mm/0.2 mm) | 0.91 | Δ |
| 57 | | | | 9 (4.5 mm/0.5 mm) | 2.43 | ○ |
| 58 | | | | 4 (4.0 mm/1.0 mm) | 5.48 | ◎ |
| 59 | | 1000 | 44.7 | 62 (4.92 mm/0.08 mm) | 0.72 | Δ |
| 60 | | | | 24 (4.8 mm/0.2 mm) | 1.86 | ◎ |
| 61 | | | | 9 (4.5 mm/0.5 mm) | 4.97 | ◎ |
| 62 | | | | 4 (4.0 mm/1.0 mm) | 11.2 | ○ |
| 63 | | | | 1.5 (3.0 mm/2.0 mm) | 29.8 | Δ |
| 64 | | 1400 | 87.7 | 62 (4.92 mm/0.08 mm) | 1.41 | Δ |
| 65 | | | | 24 (4.8 mm/0.2 mm) | 3.65 | ◎ |
| 66 | | | | 9 (4.5 mm/0.5 mm) | 9.74 | ◎ |
| 67 | | | | 4 (4.0 mm/1.0 mm) | 21.9 | ○ |
| 68 | | | | 1.5 (3.0 mm/2.0 mm) | 58.5 | Δ |
| 69 | | 1800 | 145.0 | | | Δ |
| 70 | 10.0 | 500 | 14.0 | 24 (4.8 mm/0.2 mm) | 0.58 | Δ |
| 71 | | | | 9 (4.5 mm/0.5 mm) | 1.56 | ○ |
| 72 | | | | 4 (4.0 mm/1.0 mm) | 3.50 | ○ |
| 73 | | 700 | 27.4 | 24 (4.8 mm/0.2 mm) | 1.14 | ○ |
| 74 | | | | 9 (4.5 mm/0.5 mm) | 3.04 | ◎ |
| 75 | | | | 4 (4.0 mm/1.0 mm) | 6.85 | ◎ |
| 76 | | 1000 | 55.9 | 24 (4.8 mm/0.2 mm) | 2.33 | ◎ |
| 77 | | | | 9 (4.5 mm/0.5 mm) | 6.21 | ◎ |
| 78 | | 1400 | 109.6 | 24 (4.8 mm/0.2 mm) | 4.57 | ◎ |
| 79 | | | | 9 (4.5 mm/0.5 mm) | 12.2 | ◎ |
| 80 | | | | 4 (4.0 mm/1.0 mm) | 27.4 | Δ |
| 81 | | 1800 | 181.2 | | | X |

As can be seen from Table 2, if the inner diameter (R2) and the speed of revolution (N) of the chemical agent retainer are set so that the centrifugal effect (G) exerted on the chemical agent retainer falls within the range of 10 to 150 (m/s$^2$), at least a predetermined level of insect killing effect is obtained. Furthermore, if the thickness ratio (P) is set to a value of more than 1.5 and not more than 50, and the centrifugal vaporizing/discharging index (T) is set to a value of more than 1.1 and less than 22, a more excellent insect killing effect is obtained. In contrast to this, if the thickness (B) of the chemical agent retention layer is small, and the thickness ratio (P) is more than 50, as in test nos. 59 and 64, the chemical agent retention capability of the chemical agent retainer is insufficient, and therefore, the exertion of the insect killing effect is likely to be impaired. Furthermore, if the thickness (A) of the gas permeable layer is small, and the thickness ratio (P) is not more than 1.5, as in test nos. 63 and 68, a stirred air flow caused by the gas permeable layer is nonbiting midges, flies, drain flies, clothes moths, and the like, and are also applicable to applications of controlling creeping insect pests such as cockroaches, ants, centipedes, spiders, and the like.

REFERENCE SIGNS LIST

10 chemical agent retention layer
11 interstice
20 gas permeable layer
21 void
30 form maintenance layer
50 (51, 52) chemical agent retainer
60 rotational drive part
70 rotating cartridge
100, 200 chemical agent vaporizing/discharging device

The invention claimed is:

1. A chemical agent vaporizing/discharging device comprising:

a chemical agent retainer having a chemical agent retention layer including interstices for allowing retention of a volatile chemical agent, and a gas permeable layer including voids having a size larger than a size of the interstices; and a rotational drive part for driving the chemical agent retainer, wherein a shape and a size of the chemical agent retainer, and a rotational speed of the rotational drive part, are set so that a centrifugal effect of 10 to 150 (G) is obtained during rotation of the chemical agent retainer, the chemical agent retainer is set so that the ratio (P=A/B) of a thickness (A) of the gas permeable layer to a thickness (B) of the chemical agent retention layer is not less than 3 and not more than 24, and the rotational speed of the rotational drive part is set so that a centrifugal vaporizing/discharging index (T=G/P) obtained by dividing the centrifugal effect (G) by the ratio (P) is not less than 1.14 and not more than 21.9, the chemical agent retainer has a form maintenance layer for maintaining a form of the gas permeable layer, the form maintenance layer being disposed adjacent to the gas permeable layer, and the form maintenance layer is interwoven with fibers included in the gas permeable layer.

2. The chemical agent vaporizing/discharging device according to claim 1, wherein the chemical agent retainer is a laminate of the chemical agent retention layer and the gas permeable layer, and the chemical agent retention layer is provided one or both sides of the gas permeable layer in a lamination direction.

3. The chemical agent vaporizing/discharging device according to claim 1, wherein the chemical agent retainer is in the shape of a disc perpendicular to an axis of rotation.

4. The chemical agent vaporizing/discharging device according to claim 1, wherein the chemical agent retainer is in the shape of a hollow cylinder parallel to an axis of rotation.

5. The chemical agent vaporizing/discharging device according to claim 1, wherein the chemical agent retainer is housed in a rotating cartridge coupled to the rotational drive part.

6. The chemical agent vaporizing/discharging device according to claim 1, wherein the volatile chemical agent contains a pyrethroid compound having a vapor pressure of $2\times10^{-4}$ to $1\times10^{-2}$ mmHg at 30° C.

* * * * *